(12) United States Patent
Banks

(10) Patent No.: US 6,319,481 B1
(45) Date of Patent: Nov. 20, 2001

(54) STERILIZATION CONTAINER

(76) Inventor: Percival C. Banks, 1301 Quarry Ct., Suite 204, Pt. Richmond, CA (US) 94801

( * ) Notice: Subject to any disclaimer, the term of this patent is extended or adjusted under 35 U.S.C. 154(b) by 0 days.

(21) Appl. No.: 09/809,943

(22) Filed: Mar. 14, 2001

Related U.S. Application Data

(60) Provisional application No. 60/189,232, filed on Mar. 14, 2000.

(51) Int. Cl.⁷ ........................................................ A61L 2/00
(52) U.S. Cl. .......................... 422/300; 422/298; 422/108
(58) Field of Search ................................... 422/300, 298, 422/108

(56) References Cited

U.S. PATENT DOCUMENTS

| | | | | |
|---|---|---|---|---|
| 4,617,178 | * | 10/1986 | Nichols | 422/310 |
| 4,783,321 | * | 11/1988 | Spence | 422/300 |
| 5,352,416 | * | 10/1994 | Wagner | 422/108 |

* cited by examiner

Primary Examiner—Robert J. Warden, Sr.
Assistant Examiner—Sean Conley
(74) Attorney, Agent, or Firm—H. Michael Brucker

(57) ABSTRACT

A sterilization container having off-set vents in the lid and floor where the floor vents are disposed in slopping areas of the floor that are above a fluid collection area.

11 Claims, 3 Drawing Sheets

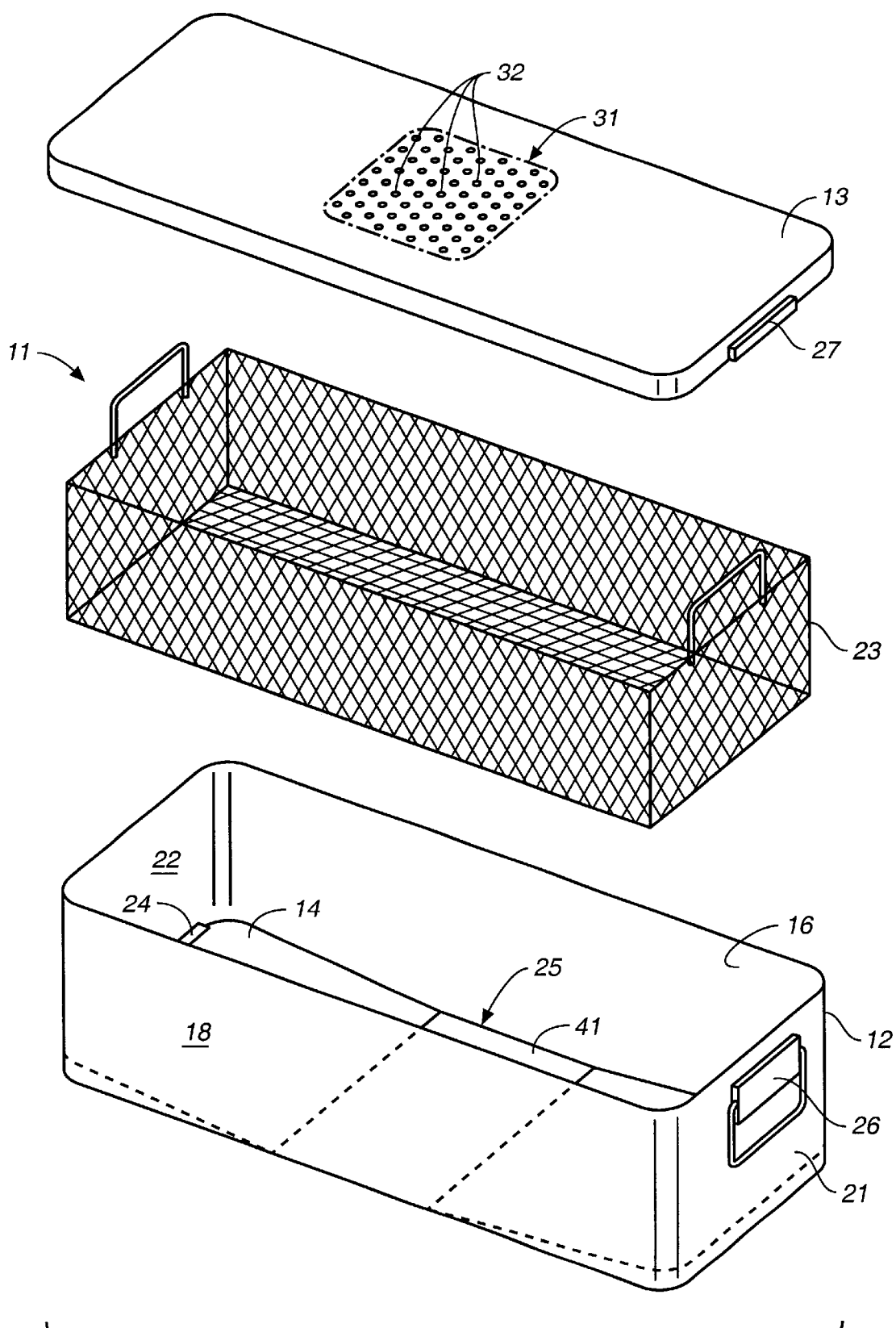
FIG._1

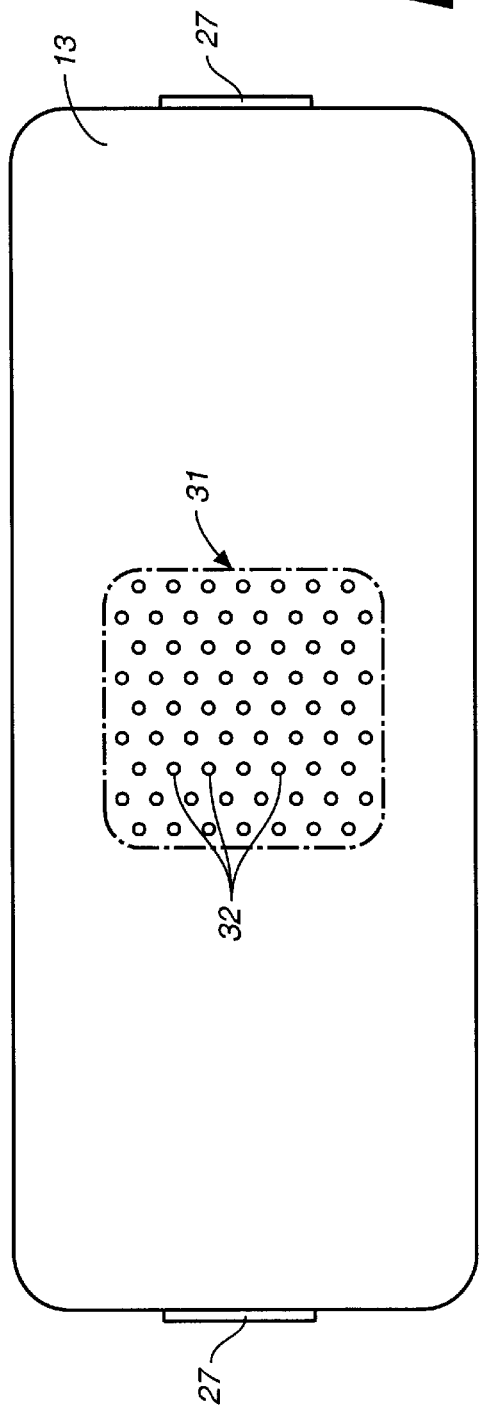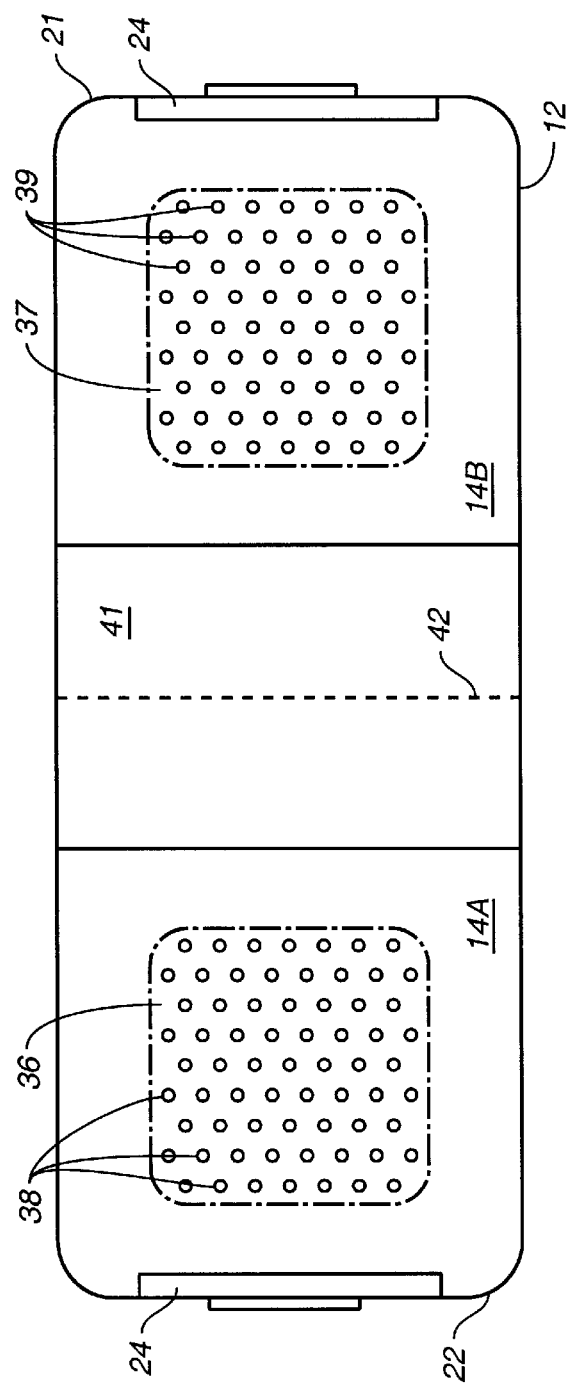

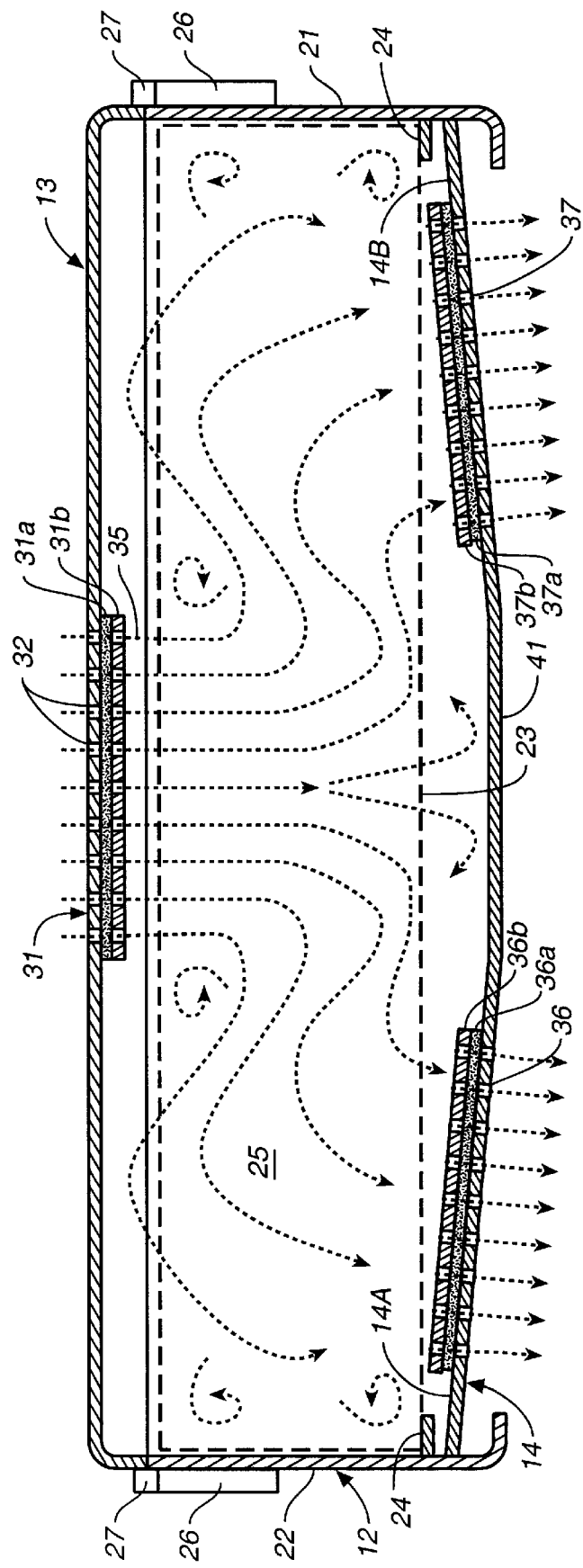
FIG._4

STERILIZATION CONTAINER

This application claims benefit to U.S. provisional application Ser. No. 60/189,232, Mar. 14, 2000.

BACKGROUND OF THE INVENTION

Acute care providers rely on various types of sterilization equipment in conjunction with established procedures to provide contamination-free perioperative care. Further, there are many regulations regarding sterilization and other aseptic practices that acute care providers must comply with. Compliance with these regulations is time-consuming and expensive, but necessary for providing quality health care. In addition, existing sterilization protocols and aseptic requirements are not universally consistent and can vary within each health care facility.

Consequently, there exists in the art different protocols which correspond to a variety of sterilization equipment and methodology regarding the processing of sterile supplies within an acute care facility. The majority of acute care facilities utilize rigid containers wherein surgical instruments and supplies are placed for sterilization, storage and transport. Depending on the processing requirements, acute care facilities must use a variety of container designs and protocols to sterilize instruments and supplies. Examples of such protocols include, but are not limited to: ETO gas, standard steam and flash autoclaving, as well as alternative low temperature methods of sterilization. All of the preceding protocols are well known within the art.

Depending on the method of sterilization, a specific type of sterilant (steam, ETO, Plasma gas, etc.) is introduced under controlled conditions (usually within a chamber) into the sealed container to eliminate microorganisms within, around and on the contents. After sterilization and prior to use, sealed containers serve as a protective repository for storage and transport of the sterilized contents. The majority of conventional sterilization containers are generally rectangular in shape wherein the lid is normally vented with a patterned group of small holes. Occasionally, the bottom of the container will also have vents aligned to mirror the placement of the vents in the lid. Each vent has a filter that allows the entry and exit of the sterilant during the sterilization cycle. After sterilization, the filters provides a protective bacterial barrier which maintains the sterile integrity of the contents during storage and transport.

However, the arrangements of filtered vents known in the art have certain disadvantages. Where vents are present only on the lid, sterilant must enter and exit through the same pathway(s). This can inhibit the introduction, dispersal and exposure of the sterilant throughout the sealed container. The inadequacy of this vent configuration is particularly deficient to meet flash gravity requirements.

Where vents are present on the bottom of the container as well as the lid, the sterilant enters and exits in a column that is created by the direct alignment of the vents in the lid and bottom. This column effect can create "dead spots" within the sealed container whereby the sterilant does not come into sufficient contact to sterilize all of the contents. Most notably, "dead spots" can occur in the corners and along the walls of the container.

Another disadvantage of conventional sterilization containers is fluid retention associated with standard autoclaving, alternative low temperature and especially flash sterilization methods. As the sterilizing media is introduced into the sealed container, condensation forms and collects on the flat (or level) floor of the container. Consequently, instruments located at (or near) the bottom of the container are at risk of corroding due to prolonged contact with the retained condensate.

If the bottom of the container is vented, the barrier properties of filters can be deficient immediately after the door of the sterilizer is opened. This situation is especially a concern when retained moisture is present and the containers are handled or transported while they are still hot. Following the "cool down" period, containers with vented bottoms are also at risk of contamination when retained moisture comes into prolonged contact with the filter elements.

Because of the substantial concern among perioperative professionals over retained moisture, existing containers are seriously limited and inappropriate for the multiple sterilization methods utilized by acute care facilities. The concern regarding retained moisture in sterilization containers is universally applicable to flash sterilization protocols. Since flash sterilization protocols do not have an adequate drying cycle, retained moisture is a normal condition in both frequency (as in always) and magnitude (as in ample) for each and every flash sterilization cycle. This condition is commonly known within the art as "wet packs."

SUMMARY OF THE INVENTION

In the present invention, a generally universal sterilization container is provided with vent holes in both the lid and the bottom of the container, but offset so that sterilant flows throughout the container between the time it enters and exits. In addition, the bottom of the container is sloped toward a center area so that all fluids flow away from the filters that cover the vents in the bottom of the container. The unique combination of design features embodied in the multipurpose sterilization container of the present invention offer enhanced performance, as well as providing a consistent protocol for use with a variety of processing methods, including flash gravity sterilization.

Accordingly, it is an object of the present invention to provide an all-purpose sterilization container in which the vent configuration promotes a distribution of sterilant throughout the container and to all items being sterilized.

It is a further object to provide a container having a floor with areas that slope way from the container end walls to a lower collection area where condensed fluids are drawn away from the sloping areas.

Yet another object of the invention is to prevent vent filters from being exposed to standing fluids by disposing the vents that the filters cover in the sloping areas of the container floor.

Still another object of the invention is to prevent items being sterilized from being in contact with standing fluids by supporting them above the fluid collection area of the container floor.

These and other objects, aspects and features of the present invention will be better understood from the following detailed description of the preferred embodiments when read in conjunction with the appended drawing figures.

BRIEF DESCRIPTION OF THE DRAWINGS

FIG. 1 is an exploded perspective view of the sterilization container of the present invention shown in relation to a basket or tray for holding and handling items to be sterilized;

FIG. 2 is a lid view of the lid of the container with the vents shown without filters or filter covers;

FIG. 3 is a plan view of the body of the container shown without filters or filter covers; and FIG. 4 is a cross-sectional side view of the container shown with filters and filter covers.

DETAILED DESCRIPTION OF THE DRAWINGS

It is to be understood that the present invention can and should vary in dimension depending in part on the size, shape and mass of the instruments and supplies to be sterilized. Further, the present invention may be constructed from a number of materials including, but not limited to, plastic, metal or any combination thereof, so long as the material is resistant to conditions common to current (and future) sterilization methods. Materials suitable for use in sterilization containers are well known in the art and include plastics and metals of various specifications.

Referring to FIG. 1, the sterilization container 11 of the present invention includes a container body 12 and a container lid 13. The container body has a floor 14, side walls 16 and 18, and end walls 21 and 22 which circumscribe a volume 25 into which a carrier (or tray) 23 is placed for holding and transporting instruments and other items to be sterilized (not shown). When fully inserted into the container body 12, the carrier 23 sits on supports 24 (see FIGS. 3 and 4) which are either attached to or molded into the walls of the container body 12 at locations that support the carrier above the floor 14.

The lid 13 attaches and is secured tightly to the body 12 by latching handles 26 and lid locks 27 (which are shown schematically only). Numerous configuration of latching handles and lid locks are well known in the art and, as such, do not form a part of the present invention. See, for example, U.S. Pat. No. 4,915,913.

The lid 13 includes a centrally located lid vent 31 formed by a plurality of vent holes 32 that occupy approximately one-third of the surface area of the lid 13. Although the illustrated vent 31 has a square pattern of round holes 32, the geometry of the pattern and holes can vary without departing from the invention provided the vent 31 is centrally located on the lid 13. During the sterilization cycle, sterilant enters the interior of the container via the vent holes 32.

Two floor vents 36 and 37 formed by vent holes 38 and 39, respectively, are located in the floor 14 of the container body 12 at locations proximal to end walls 21 and 22 and not vertically aligned with the lid vent 31 when the lid 13 is secured to the body 12. In the preferred embodiment, the bottom vents 36 and 37 are approximately the same size and shape as the lid vent 31, although the benefits of the invention can be realized with vents of different sizes and shapes. The major benefits of the invention are realized by having the lid vent 31 centrally located in the lid 13 and the floor vents 36 and 37 laterally displaced from the lid vent 31—not vertically aligned therewith—when the lid 13 is secured to the container body 12. In this way, sterilant entering the lid vent 31 will more likely occupy the entire volume 25 of the container body 12 before exiting the bottom vents 36 and 37.

Referring to FIG. 4, as is standard practice in the art, a filter element 31a is placed across vent 31 and is held in place by a filter cover 31b that contains a patterned grouping of holes through which sterilant can pass. Similarly, vents 36 and 37 are covered by filters 36a and 37a, respectively, and held in place by filter covers 36b and 37b. The filter covers 31b, 36b and 37b are securely held in place by means well known in the art (not shown) that do not form a part of the invention.

The dispersal of the sterilant completely and consistently throughout the interior of the sealed container occurs by virtue of gravity, pressure and/or thermodynamics; whereby the sterilant exits the container via the two laterally positioned floor vents in the floor of the container.

The flow pattern 35 of the sterilizing media as it enters and exits the interior of the container includes all of the volume 25. This flow pattern insures the expeditious and complete dispersal of sterilant throughout the sealed container. The number, size, location, and positional relationship of the filtered vents 31, 36 and 37 make this possible. These features combine to create the exceptional performance benefits of this invention. The centrally located vent 31 in the lid provides a dedicated entry port for the sterilant. The vents 36 and 37 located in the floor 14 adjacent the end walls 21 and 22 provide two dedicated exit paths that offer twice the vapor exchange capacity of the single entry vent 31 in the lid 13. This design insures proper dispersal, along with an enhanced flow rate of the sterilant throughout the container, by eliminating back pressure (typical of those containers with vents only in the lid) and the elimination of "dead spots" typical of existing containers with opposing (vertically aligned) vents in the lid and bottom where the sterilant traverses the interior of the container in a column from lid to floor.

In addition to the relative placement of the vents 31, 36 and 37, the portions 14a and 14b of the floor where the vents 36 and 37 are located slope downward away from each end wall 21 and 22 towards the center of the container body 12. The sloped portions 14a and 14b of floor 14 terminates short of the midline 42 of the floor 14 (see FIG. 3) where they connect to a level collection portion 41 between the sloped portions 14a and 14b.

Accordingly, condensation in the form of retained moisture is directed towards the central collection portion 41 and away from the filters 36a and 37a. Because the basket or tray holding the contents to be sterilized is supported above the center collection portion 41, the risk of instrument corrosion from prolonged direct exposure to retained moisture is eliminated.

Furthermore, the risk of contamination caused by retained moisture is eliminated by the location of the filtered vents 36 and 37 in the sloped portions 14a and 14b of the floor 14. This sloped configuration of the floor 14 directs moisture away from the vents 36 and 37, thereby preventing moisture from coming into sustained contact with the filter elements 36a and 37a. This feature ensures the protective barrier qualities of the filter elements 36a and 37a, thereby maintaining the sterile integrity of the contents.

The center collection portion 41, or a part thereof, may be made of a material that facilitates the evaporation of any retained moisture. For example, if the container were made of plastic, in the preferred embodiment, the collection portion 41 would be entirely or partially comprised of a more heat absorbent material such as metal. This feature helps to eliminate retained moisture through vaporization as it comes in contact with the heated portion of the collection portion 41.

Of course, various changes, modifications and alterations in the teachings of the present invention may be contemplated by those skilled in the art without departing from the intended spirit and scope thereof. As such, it is intended that the present invention only be limited by the terms of the appended claims.

What is claimed is:

1. In a sterilization container having a body formed by a floor, two side walls and two end walls which define a volume for receiving a sterilant and into which a sterilization tray can be disposed, and also having a lid which, when secured to the body, encloses the volume, the improvement comprising:

a vent centrally located in the lid through which sterilant can pass;

the body floor having sloping portions adjacent the end walls; and vents located in said sloping portions of the floor.

2. The sterilization container improvement of claim 1 wherein the floor has a collection portion between and below said sloping portions.

3. The sterilization container improvement of claim 2 further comprising:

supports on the body portion which support a sterilization tray above said sloping portions of the floor.

4. The sterilization container improvement of claim 2 wherein said lid vent and said floor vents are all approximately the same size.

5. The sterilization container improvement of claim 4 wherein said lid vent occupies approximately one-third the area of the lid.

6. The sterilization container improvement of claim 4 wherein said lid vent and said floor vents are formed by a pattern of holes.

7. The sterilization container improvement of claim 2 wherein said collection portion includes a material of high heat conductivity.

8. A sterilization container comprising in combination;

a body formed by a floor, two side walls and two end walls wherein said floor includes a sloping portion extending from each end wall and connecting to a central collection portion therebetween and therebelow;

a lid securable to said body;

a lid vent centrally located in said lid; and a floor vent located in each of said sloping portions and not aligned with said lid vent when said lid is secured to said body.

9. The sterilization container of claim 8 wherein said lid vent is formed by holes that occupy approximately one-third the area of said lid and said floor vents are approximately the same size and shape.

10. The sterilization container of claim 9 wherein said central collection area includes a material of relatively high heat conductivity.

11. The sterilization container of claim 10 wherein said central collection area includes a material of relatively high heat conductivity.

* * * * *